(12) United States Patent
Grieco et al.

(10) Patent No.: US 6,210,638 B1
(45) Date of Patent: Apr. 3, 2001

(54) PLASTIC STERILIZATION CASE

(75) Inventors: Gerard Grieco, Towaco; Ignazio Graziano, Paramus, both of NJ (US)

(73) Assignee: Jewel Precision, Ceder Grove, NJ (US)

( * ) Notice: Subject to any disclaimer, the term of this patent is extended or adjusted under 35 U.S.C. 154(b) by 0 days.

(21) Appl. No.: 09/045,145

(22) Filed: Mar. 20, 1998

(51) Int. Cl.[7] ...................................................... A61L 2/08
(52) U.S. Cl. ........................ 422/22; 220/345.1; 422/297; 422/300
(58) Field of Search .............................. 422/22, 292, 297, 422/300; 206/503, 508; 220/345.2, 345.3, 350, 351, 345.4, 345.1; 435/305.4

(56) References Cited

U.S. PATENT DOCUMENTS

| | | | | |
|---|---|---|---|---|
| 2,064,241 | * | 12/1936 | Batdorf ................................... | 220/41 |
| 2,083,356 | * | 6/1937 | Batdorf ................................... | 220/41 |
| 2,093,508 | * | 9/1937 | Batdorf ................................... | 220/41 |
| 2,102,094 | * | 12/1937 | Romig ..................................... | 220/41 |
| 3,782,584 | * | 1/1974 | Swenson et al. ....................... | 220/41 |
| 3,854,649 | * | 12/1974 | Wagner et al. ......................... | 220/41 |
| 4,405,057 | * | 9/1983 | Stein ...................................... | 220/346 |
| 4,470,518 | * | 9/1984 | Stein ...................................... | 220/346 |
| 4,535,890 | * | 8/1985 | Artusi .................................... | 220/346 |
| 4,561,544 | * | 12/1985 | Reeve .................................... | 220/346 |
| 4,782,942 | * | 11/1988 | Ashley et al. ......................... | 422/300 |
| 4,946,057 | * | 8/1990 | Connolly et al. ..................... | 220/347 |
| 5,129,538 | * | 7/1992 | Bennett ................................. | 220/346 |
| 5,415,846 | * | 5/1995 | Berry, Jr. .............................. | 422/300 |
| 5,762,226 | * | 6/1998 | Baltus et al. .......................... | 220/346 |

* cited by examiner

*Primary Examiner*—Terrence R. Till
*Assistant Examiner*—Monzer R. Chorbaji
(74) *Attorney, Agent, or Firm*—Reed Smith LLP

(57) ABSTRACT

The invention comprises a sterilization case having a body having a bottom and first, second, third and fourth sidewalls upstanding from the bottom defining an interior cavity, the sidewalls having edges defining a cavity top opening; the edges of the first and second sidewalls have flanges protruding away from the interior of the cavity; a lid sized to cover the top opening and close the cavity, the lid having first an second edges corresponding to the first and second sidewalls of the body, the first and second edges having grooved members for slidably engaging the flanges, the lid being slidably movable between a closed position wherein the lid fully covers the top opening and is secured to the body by engagement of the grooved members with the flanges, and an open position ad wherein the grooved members are disengageable from the flanges and the lid is removable from the body. Methods for using the sterilization case are also disclosed.

12 Claims, 6 Drawing Sheets

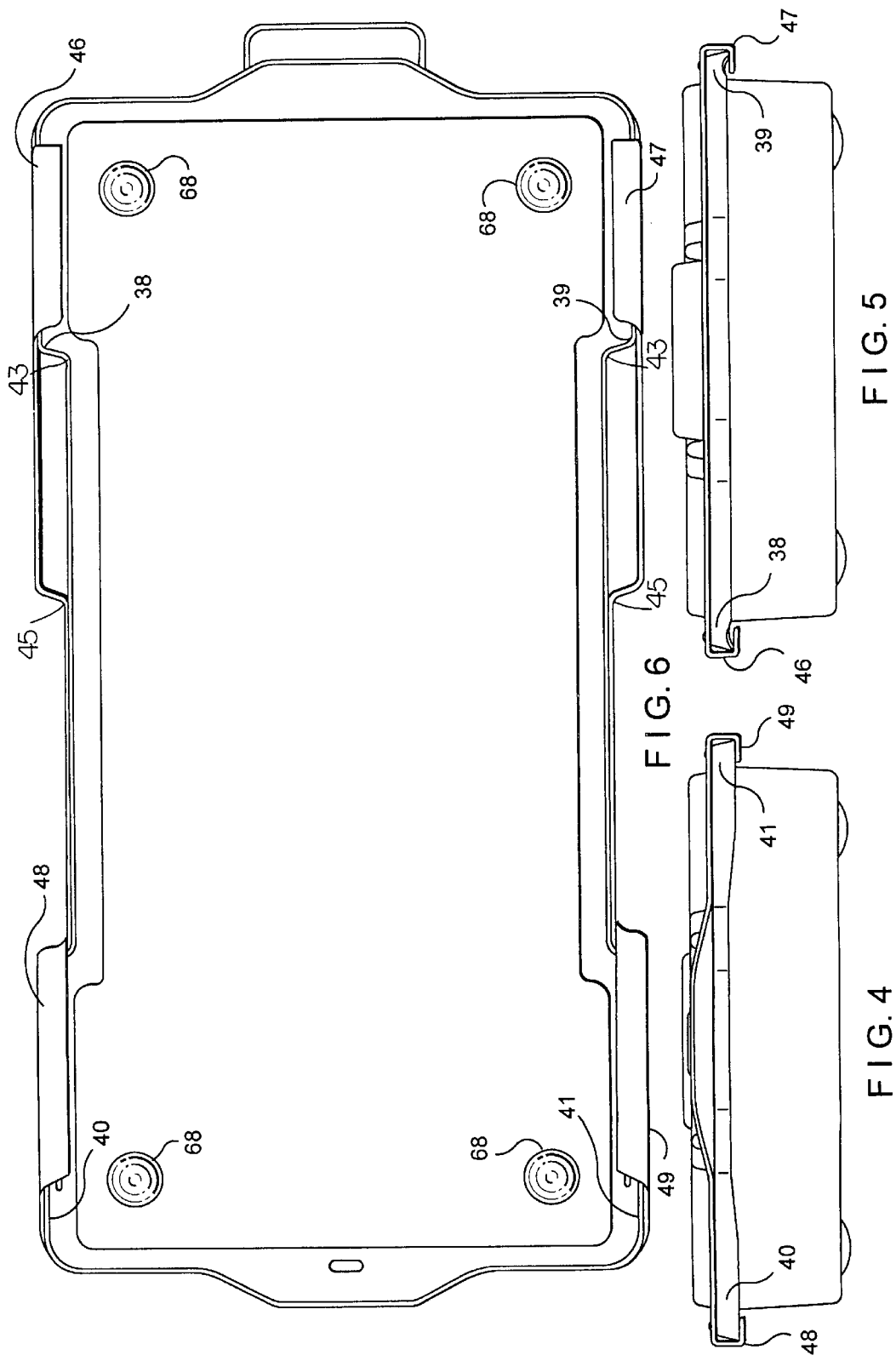

PLASTIC STERILIZATION CASE

FIELD OF THE INVENTION

The present invention relates to a sterilization case or other elements for surgical tools which does not require any exterior hardware for securing the cover to the case. Also described is a method of sterilizing surgical tools and other elements using the new sterilization case.

BACKGROUND OF THE INVENTION

Currently available of plastic sterilization cases have external metal or plastic latches attached thereto for securing a cover to the case. These latches require many moving mechanical parts to lock the case. The assembly of these latches onto cases is a very time consuming effort. Because of the many moving parts and complicated design of these latches they have a tendency to break over time. Another major problem with the existing latches is that because they are made from metal or hard plastic they have a tendency to cause the plastic in the cases to fatigue in the area where the latch grabs the material to lock it. Over time the latches will pop open if the case is dropped or banged due to the material fatigue on the cases.

Another problem with the existing cases is that the external latches protrude from the surface of the sterilization case. After a surgical procedure, instruments are repacked into the sterilization case and sterilized in the case. After the sterilization treatment, the case is wrapped in special surgical gauze to ensure sterility until the next use. Since these latches protrude from the surface of the sterilization case, they have a tendency to catch on and tear the surgical gauze, requiring resterilization of the case.

Also problematic is the amount of clearance room required to open the existing surgical sterilization cases in the often very confined space of the operating room.

SUMMARY OF THE INVENTION

Accordingly, it is an objective of this invention to provide a sterilization case having no external hardware for sterilizing, transporting and storing surgical instruments, or other elements and tools to be sterilized, which can be securely locked in a closed position.

It is another objective of the invention to provide a sterilization case having a body and mating lid which can be placed on the body and slid between an open position and a locked, closed position.

Another objective of the present invention is to provide a sterilization case with a smooth exterior which can be wrapped in surgical gauze without risk of catching or tearing the gauze.

Yet another objective of the present invention is to provide a sterilization case for surgical instruments which requires a minimum amount of clearance to open and close.

A further objective of the invention is to provide a method of sterilizing elements and surgical tools.

We have discovered a sterilization case that achieves the above objectives. The inventive sterilization case comprises a body defining an interior cavity and a lid sized to cover and close the cavity. The cavity can be of any size or shape needed to contain instruments for use in surgery or other elements to be sterilized. Integral to the body of the sterilization case are flanges which protrude from exterior sides of the body. The lid has grooved members in corresponding exterior sides for slidably engaging the flanges. The lid can be slid across the body between a closed position wherein the lid fully covers the cavity and is secured to the body by engagement of the grooved members with the flanges, and an open position wherein the grooved members are disengaged from the flanges and the lid is removable from the body.

BRIEF DESCRIPTION OF THE DRAWINGS

FIG. 4 is an end view of the sterilization case depicted in FIG. 3 from position X.

FIG. 5 is an end view of the sterilization case depicted in FIG. 3 from position Y.

FIG. 6 is a bottom view of the sterilization case of FIG. 3 from position Z.

DESCRIPTION OF THE PREFERRED EMBODIMENT

Figure 1:
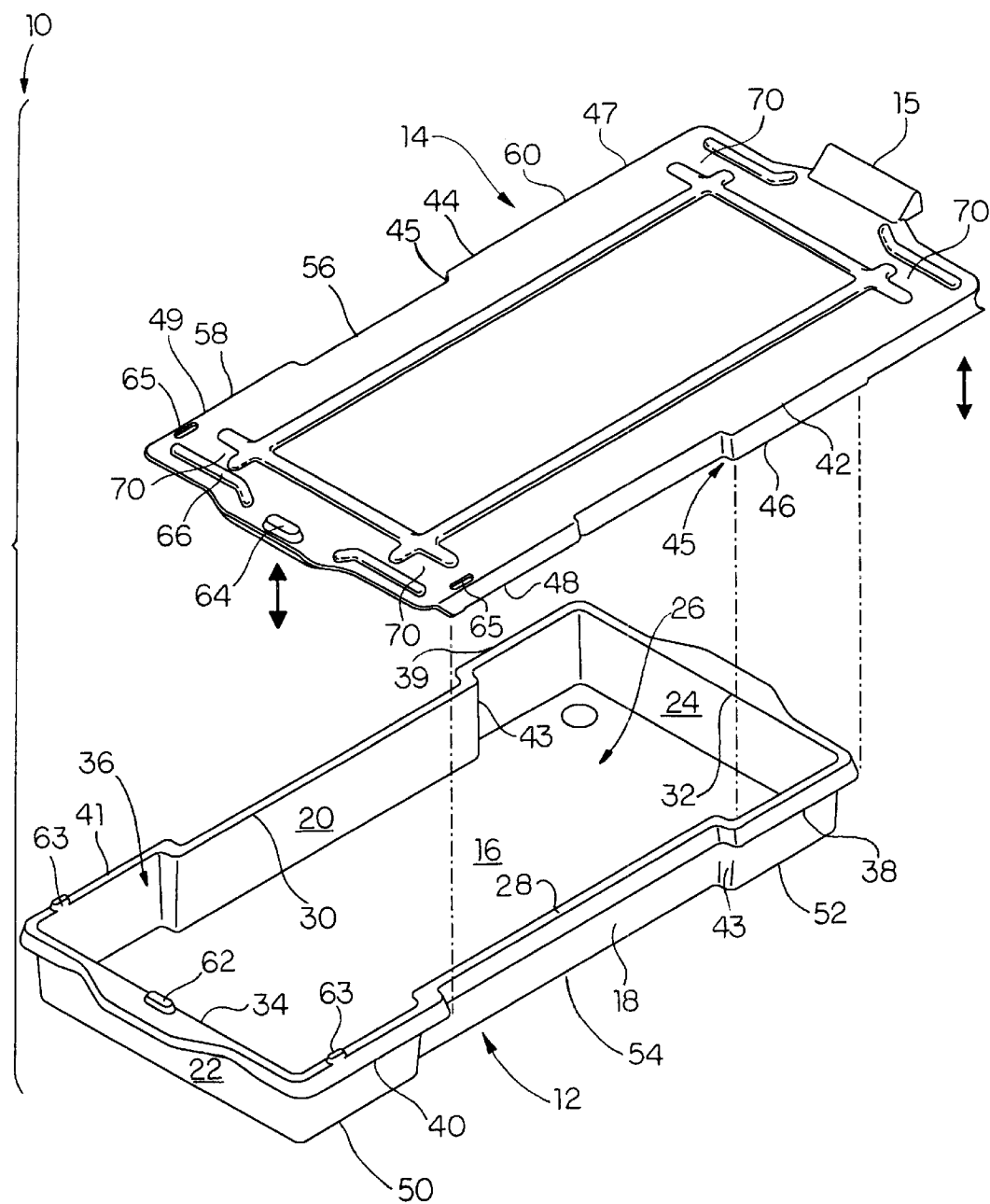
FIG. 1 is a perspective view of a sterilization case in accordance with the invention.

Referring to the drawings and in particular, FIG. 1, shown is a rectangular sterilization case having a body 12 and a lid 14. The body 12 has a bottom side 16 and first, second, third and fourth sidewalls 18, 20, 22, and 24, upstanding from bottom 16 to define an interior cavity 26. The sidewalls have edges 28, 30, 32, and 34, respectively, which define a cavity top opening 36.

Edges 28 and 30 have flanges first, second, third and fourth flanges 38, 39, 40, and 41, respectively, which protrude in a direction away from interior cavity 26.

The inventive sterilization case has a lid 14 which is sized and shaped to cover opening 36 so as to be capable of closing cavity 26. Lid 14 has first and second edges 42 and 44 corresponding to first and second sidewalls 18 and 20 of the body. The first and second edges 42 and 44 have first, second, third and fourth groove members 46, 47, 48, and 49, respectively (FIG. 4 and FIG. 5) which, when lid 14 is mounted onto body 12 as described hereinafter, and moved in the direction shown by arrow A', slidably engage flanges 38, 39, 40, and 41, respectively.

Figure 3:
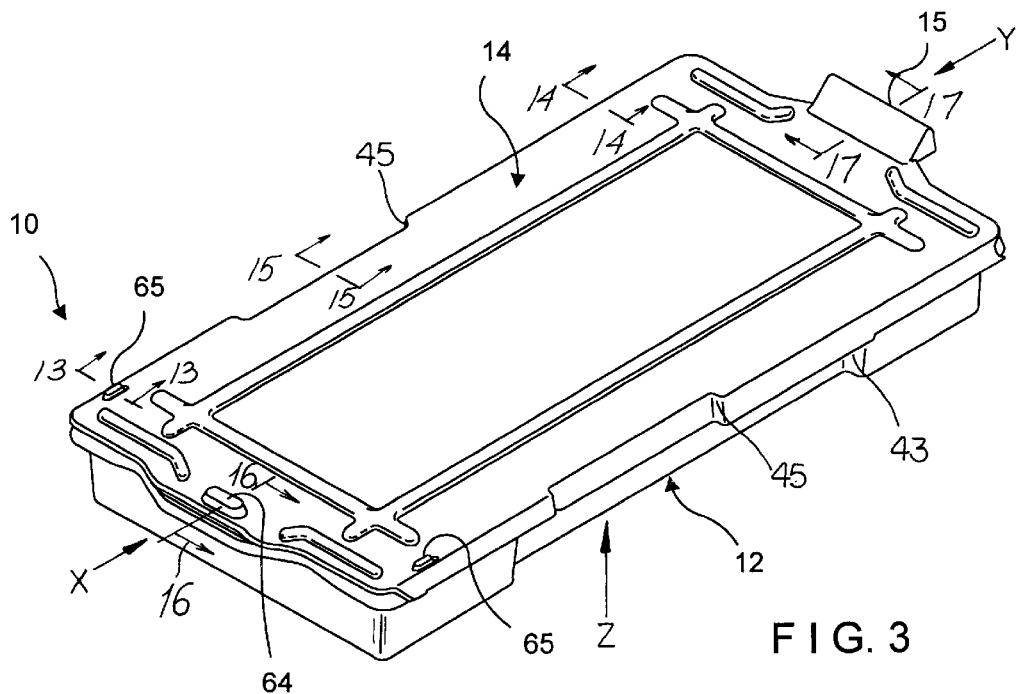
FIG. 3 is a perspective view of a sterilization case in accordance with the invention with the lid mounted on the body in the closed position.
Figure 2:
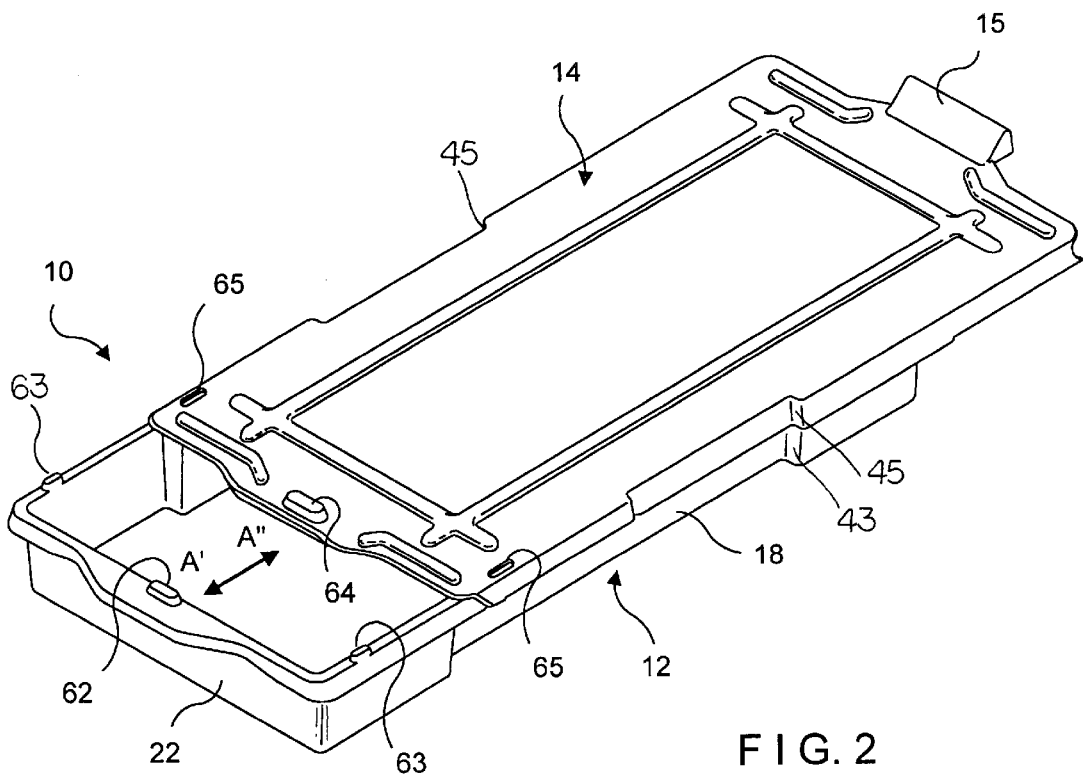
FIG. 2 is a perspective view of a sterilization case in accordance with the invention with the lid mounted on the body in the open position.

As shown in FIGS. 2 and 3, lid 14 is may be mounted onto body 12 and is slidable between an open position wherein the grooved members 46, 47, 48, and 49 are disengaged from the flanges 38, 39, 40, and 41, and the lid 14 can be removed from body 12 and a closed position as depicted in FIG. 3 wherein the grooved members 46, 47, 48, and 49, engage with flanges 38, 39, 40, and 41, respectively, thereby securing lid 14 to body 12.

As further shown in FIGS. 1, 2, and 3, body 12 may have a general rectangular shape and is composed of first and second end sections 50 and 52 and a middle section 54 which is indented, such that the middle section 54 is narrower than first and second end sections 50 and 52, and flanges 38 and 39 protrude from end section 52 and flanges 40 and 41 protrude from end section 50.

Lid 14 has a shape corresponding to the shape of the top opening 36 having an indented middle section 56 and first and second lid end sections 58 and 60. Middle section 56 is narrower than end sections 58 and 60, which correspond in size to body end sections 50 and 52, respectively, with narrower lid mid section 56 corresponding to narrower body middle section 54. Groove members 46 and 47 are attached to second end section 60 and groove members 48 and 49 are attached to first end section 58 of lid 14.

As shown clearly in FIG. 4, FIG. 5, and FIG. 6, which is a bottom view of the inventive case with the lid 14 in the closed position and secured onto body 12, first, second, third and fourth groove members 46, 47, 48, and 49, engage first, second, third and fourth flanges 38, 39, 40 and 41, respectively, and the lid 14 fully covers the cavity top opening 36.

Figure 8:
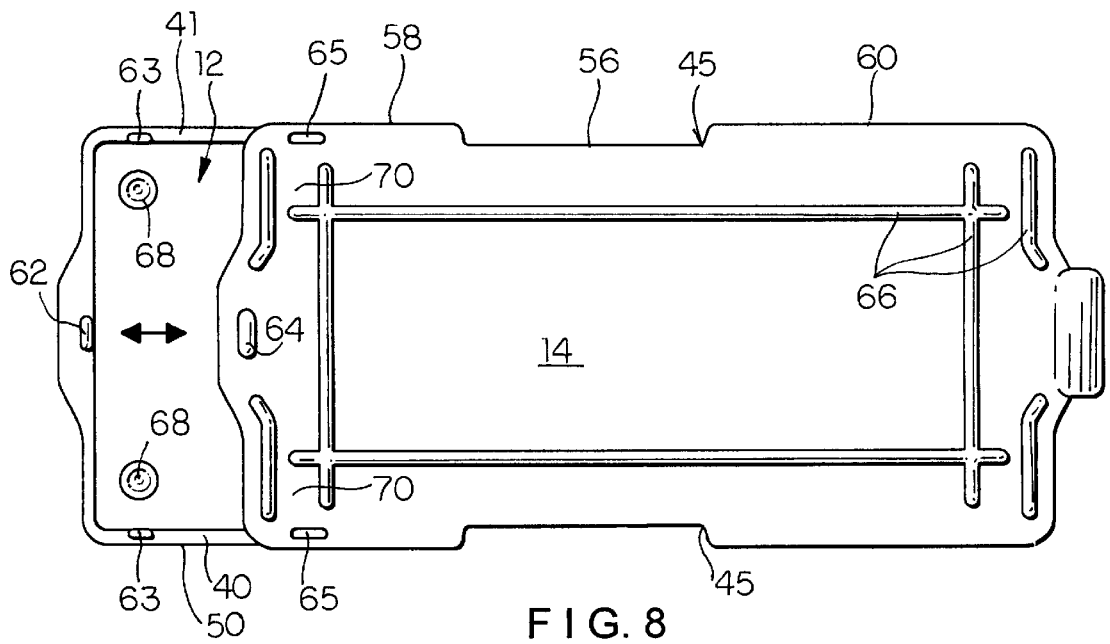
FIG. 8 is a top view of the sterilization case of FIG. 2 from position T.

Referring to FIGS. 2, 3, and 8, the body first section 50 has protrusions 62 and 63 and lid 14 has a corresponding recess 64, and slots 65, respectively, such that when the lid is in the closed position, protrusion 62 engages recess 64 and protrusions 63 engage slots 65, thus serving to lock the lid in place.

Figure 10:
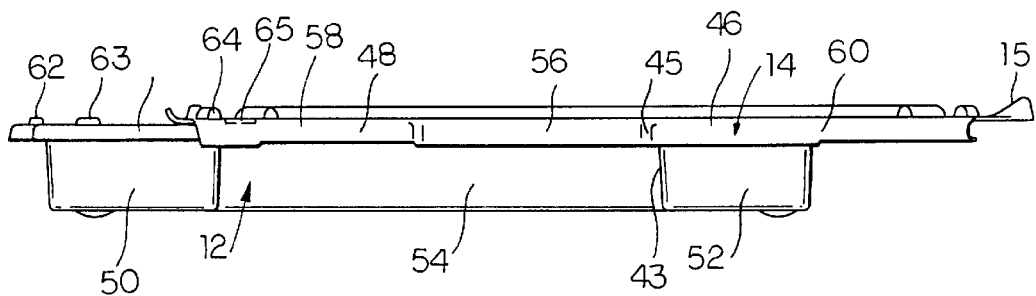
FIG. 10 is a side view of the sterilization case of FIG. 2 from position $S_2$.
Figure 10A:
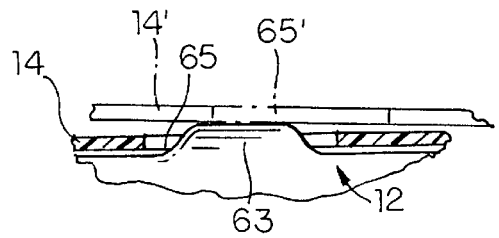
FIG. 10A is a detail from FIG. 10 showing the movement of the lid over protrusions 63.
Figure 16:
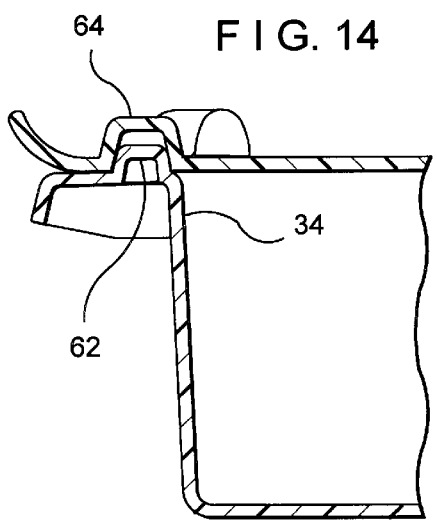
FIG. 16 is a detailed cross-sectional view along the line 16—16 of FIG. 3.
Figure 17:
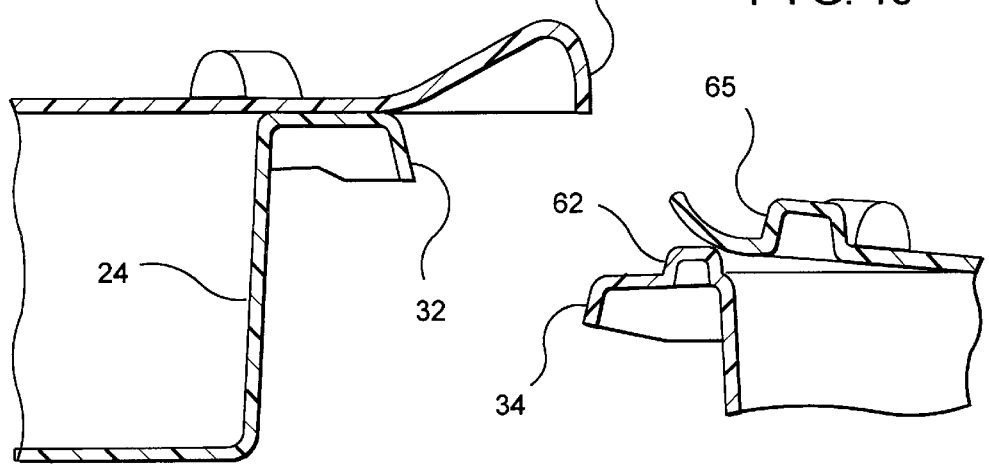
FIG. 17 is a detailed cross-sectional view along the line 17—17 of FIG. 3.
Figure 18:
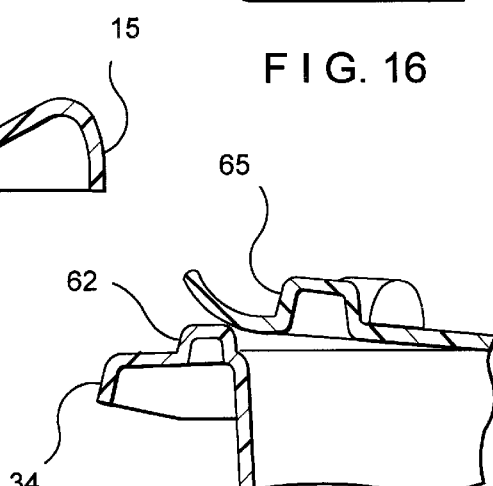
FIG. 18 is a detailed cross-sectional view showing the positioning of lip 67 just prior to engagement with protrusion 62.

Lid 14 has a degree of flexibility such that as it is moved in the direction of arrow A', it can slid over protrusions 62 and 63 as shown in FIGS. 10A and 18.to lock the lid in place. Conversely, when the lid is moved in the reverse A", it is sufficiently flexes so to disengage from the respective protrusions 62 and 63. The lid may have an upwardly curved lip portion 67 (shown in FIGS. 2 and 11) which serves to ease the lid up and over protrusion 62 as the lid is being moved into the closed position. FIG. 18 shows lip 67 as it is moving up and over protrusion 62 and FIG. 16 shows protrusion 62 and recess 64 engaged.

As further shown in FIG. 1, the lid may have reinforcing rails or embosses 66 therein which serve to stabilize the lid from warping and serve to retain it in a planar shape.

Figure 7:
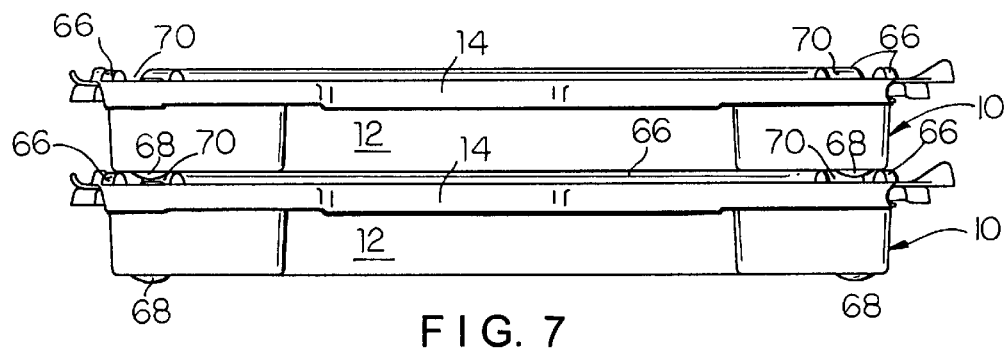
FIG. 7 is a side view of stacked inventive sterilization cases.

In addition, as shown in FIGS. 4, 5, and 6, bottom side 16 has at its respective corners, protrusions 68 and lid 14 has corresponding recesses 70 which may be created by the design of the reinforcing rails. The protrusions 68 and recesses 70 serve to allow stacking of a plurality of sterilization cases and to help retain the cases one upon the other in the stacked position as shown in FIG. 7.

Figure 11:
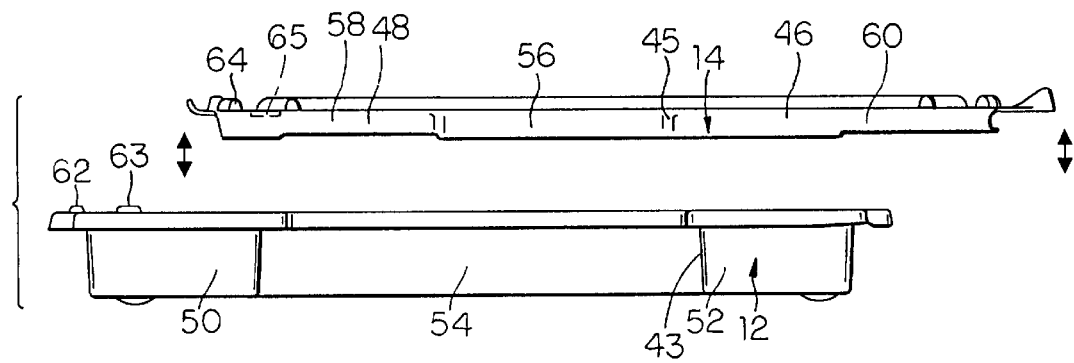
FIG. 11 is a side view of the sterilization case of FIG. 1 from position $S_3$.
Figure 12:
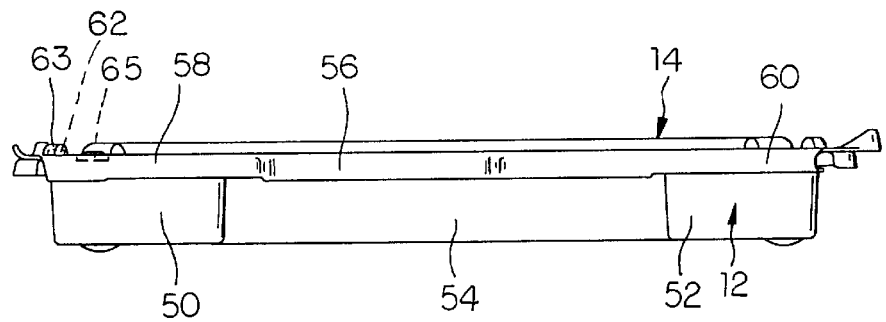
FIG. 12 is a side view of the sterilization case of FIG. 3 from position $S_1$.
Figure 13:
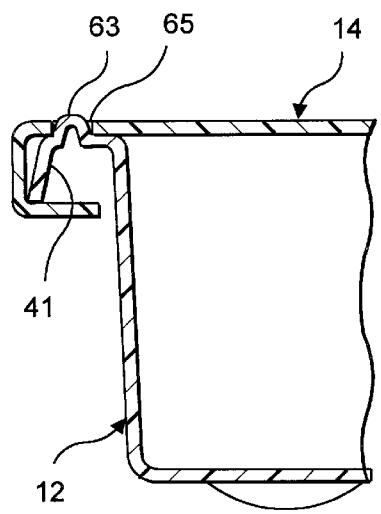
FIG. 13 is a detailed cross-sectional view along the line 13—13 of FIG. 3.
Figure 14:
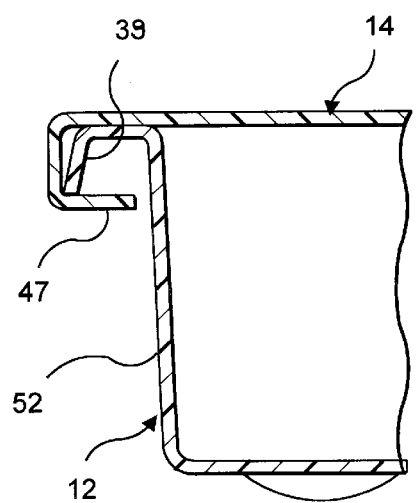
FIG. 14 is a detailed cross-sectional view along the line 14—14 of FIG. 3.
Figure 15:
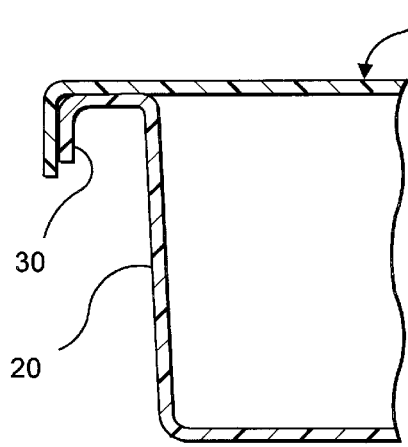
FIG. 15 is a detailed cross-sectional view along the line 15—15 of FIG. 3.

As shown in FIG. 1 and FIG. 11, the lid 14 may be mounted onto the body 16 from a vertical position along the direction of arrow B'–B". This is important in that it means that the lid does not have to be fully extended from the body which would basically triple the horizontal room required to mount the lid on the body. Rather, the lid may be displaced from the body only by approximately ¼ to ⅓ of the body length and vertically positioned onto the body as depicted by the phantom lines shown in FIG. 1. The positioning of the lid upon mounting is shown in FIG. 2. The lid is then slid towards the protrusion in the direction of A' to allow the grooved members to engage the flanges and close the cavity opening. When pushed into the fully closed position, protrusion 62 engages recess 64 and the lid and body are locked and ready for being subjected for sterilization conditions.

Figure 9:
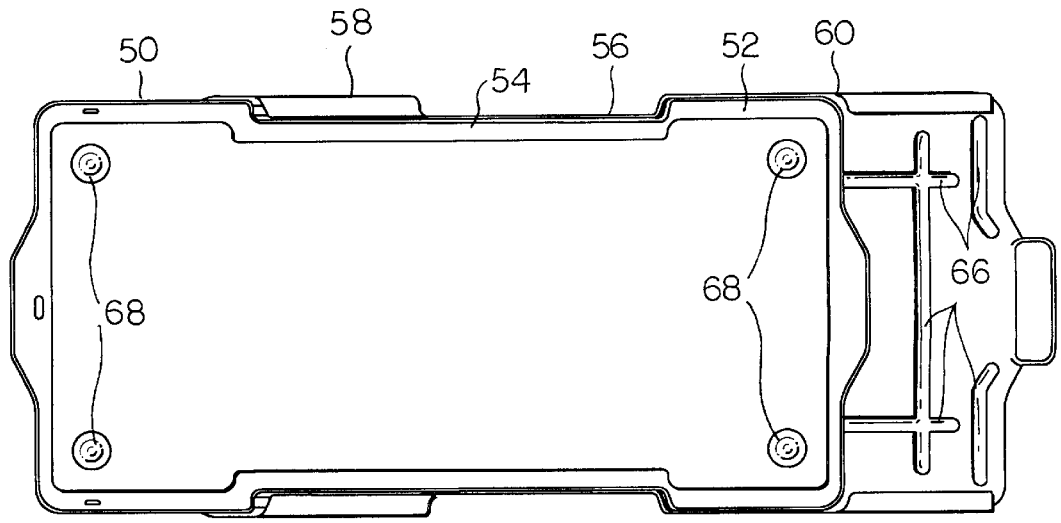
FIG. 9 is a bottom view of the sterilization case of FIG. 2 from position U.

The inventive case may also have detent means serving to limit the range of horizontal movement of the lid relative to the body as the lid is moved from the closed position to the open position. Thus, as shown in FIG. 1, FIG. 9 and FIG. 10, the narrowing of the lid from end section 60 to mid section 56 creates shoulders 45. When the lid is moved in the direction A" of FIG. 2, shoulders 45 impinge upon shoulders 43 created by the narrowing of middle section 54 of the body from the end section 52, and further horizontal movement is constrained. At this point, the lid may be lifted vertically from the body as shown in FIG. 11.

The sterilization case is opened by the reverse procedure. The lid is grasped by the handle 15 and slid horizontally across the body, with the material of the lid flexing to pass the protrusions 63, until the groove members are free of the flanges and the lid can be lifted horizontally off of the body. The shoulder 45 of the lid is placed to stop the horizontal sliding motion of opening the lid by contacting the shoulder 43 of the body once the groove members are disengaged from the flanges.

The present invention also provides a method of sterilizing surgical tools by placing them in the cavity of the body of a sterilization case according to the invention, placing the lid over the body in the open position, sliding the lid to the closed position and subjecting the case and the tools in the case to sterilizing conditions.

The sterilization case may be made from any sterilizable material. A sterilizable material is any material that can be rid of all infectious components by a sterilizing method such as heat, irradiation or chemical bath. Preferably, the case is made from medical grade, heat or irradiation sterilizable plastic, including, but not limited to, high density polymers such as acetyl copolymers, acetyl homopolymers, high density polypropylene, tetrafluroethylene and the like. Most preferably, Ultem, an amorphous thermoplastic polyetherimide resin manufactured by General Electric Plastics, or Radel, a polyphenylsulfone resin manufactured by Amoco Polymers, are used in the construction. The lid and body may be manufactured by any method. When plastics are used to construct the lid and body, the methods of thermoforming or injection molding the resin are preferred. Of course, if the sterilization is to be carried out by irradiation, the material must be permeable to the radiation used. Similarly if a chemical sterilizing bath is to be used, the case cannot be liquid tight so that sterilizing liquid will have access to the interior cavity. In the case of steam sterilization, the case must also be accessible to the steam and cannot be air or gas tight.

Other modifications and additional embodiments will be suggested to those skilled in the art upon a reading of the description of this invention. While particular embodiments of the present invention have been illustrated and described herein, they are not intended to limit the invention, except as defined in the following claims.

We claim:

1. A sterilization case comprising:
   a body having a bottom and first, second, third and fourth sidewalls upstanding from the bottom defining an interior cavity, the sidewalls having edges defining a cavity top opening; the edges of the first and second sidewalls having flanges protruding away from the interior of the cavity;
   a lid sized to cover the top opening and close the cavity, the lid having first and second edges corresponding to the first and second sidewalls of the body, the first and second edges having grooved members for slidably engaging the flanges, the lid being mountable on the body and slidably movable between a closed position wherein the lid fully covers the top opening , the grooved members and flanges engaging and cooperating with each other to secure the lid to the body in the closed position, and an open position wherein the grooved members are disengaged from the flanges, the lid partially covers the top opening and is vertically removable from the body.

2. The sterilization case of claim 1 wherein:
   the body is rectangular in shape and is composed of two end sections and an indented middle section there between, the indented middle section being narrower than the end sections;
   the flanges protrude from the side wall of the end sections,
   the lid has a shape corresponding to the shape to the top opening and has end sections and an indented middle section corresponding to the end and middle sections of the body;
   the groove members are present only in the end sections of the lid; and
   the lid is mountable onto the body from a vertical direction to partially cover the top opening, and once thus mounted on the body, is slidable horizontally with respect to the body so that the grooved members engage the flanges and can be moved to the closed position.

3. The sterilization case of claim 2 wherein the body and the lid have a protrusion and recess which cooperate to secure the lid in the closed position.

4. The sterilization case of claim 2 having detent means for stopping the lid as it is moved from the closed position when it has reached the open position and the grooved members are disengaged from the flanges so that the lid can be lifted vertically away and removed from the body.

5. The sterilization case of claim 4 wherein in the open position, the lid partially covers the top opening.

6. The sterilization case of claim 1 wherein the lid has an exterior top surface and the body has a exterior bottom surface, each of which have cooperating stacking means to allow a plurality of cases to be vertically stacked and releasably secured to one another.

7. The sterilization case of claim 1 which is made of a material which is permeable to sterilizing radiation.

8. A method for sterilizing elements wherein the elements are subjected to sterilization conditions, the improvement which comprises:
   a) placing the elements in a sterilization case comprising:
      a body having a bottom and first, second, third and fourth sidewalls upstanding from the bottom defining an interior cavity, the sidewalls having edges defining a cavity top opening; the edges of the first and second sidewalls having flanges protruding away from the interior of the cavity;
   b) mounting a lid sized on the body to cover the cavity top opening, the lid having first and second edges corresponding to the first and second sidewalls of the body, the first and second edges having grooved members for slidably engaging the flanges, the lid being mountable on the body and slidably movable between a closed position wherein the lid fully covers the top opening, the groove members and flanges engaging and cooperating with each other to secure the lid to the body in the closed position, and an open position wherein the grooved members are disengaged from the flanges, the lid partially covers the top opening and is vertically removable from the body;
   c) moving the lid to the closed position; and
   d) subjecting the elements in the case to sterilization conditions.

9. The method of claim 8 wherein the body is rectangular in shape and is composed of two end sections and an indented middle section there between, the indented middle section being narrower than the end sections,
   and wherein the flanges protrude from the side wall of the end sections,
   the lid having a shape corresponding to the shape to the top opening and having end sections and an indented middle section corresponding to the end and middle sections of the body
   and wherein the groove members are present only in the end sections of the lid;
   mounting the lid onto the body from a vertical direction to partially cover the top opening, and then, sliding the lid horizontally with respect to the body to engaged the grooved members with the flanges and move the lid to the closed position.

10. The method of claim 9 wherein the lid has an exterior top surface and the body has a exterior bottom surface, each of which have cooperating stacking means to allow a plurality of cases to be vertically stacked and releasably secured to one another.

11. The method of claim 8 wherein the body and the lid have a protrusion and recess which cooperate to secure the lid in the closed position.

12. The method of claim 10 wherein in the open position, the lid partially covers the top opening.

* * * * *